(12) United States Patent
Forman

(10) Patent No.: US 10,329,594 B1
(45) Date of Patent: Jun. 25, 2019

(54) CELL LINES FOR HIGH LEVEL PRODUCTION OF PROTEIN-BASED PHARMACEUTICALS

(71) Applicant: CHO Plus Inc., San Francisco, CA (US)

(72) Inventor: Lawrence Forman, San Francisco, CA (US)

(73) Assignee: CHO Plus, Inc., San Francisco, CA (US)

(*) Notice: Subject to any disclaimer, the term of this patent is extended or adjusted under 35 U.S.C. 154(b) by 118 days.

(21) Appl. No.: 15/254,852

(22) Filed: Sep. 1, 2016

Related U.S. Application Data

(60) Provisional application No. 62/213,880, filed on Sep. 3, 2015.

(51) Int. Cl.
*C12P 21/00* (2006.01)
*C07K 16/00* (2006.01)
(Continued)

(52) U.S. Cl.
CPC .............. *C12P 21/00* (2013.01); *C07K 16/00* (2013.01); *C12N 5/16* (2013.01); *C12N 5/163* (2013.01);
(Continued)

(58) Field of Classification Search
CPC ........ C12P 21/00; C12P 21/005; C07K 16/00; C07K 2317/14; C07K 2317/51; C07K 2317/515; C12N 5/16; C12N 5/163; C12N 2510/02; C12Y 301/03001; G01N 33/5005; G01N 33/5076; G01N 33/56966; G01N 2333/916
See application file for complete search history.

(56) References Cited

U.S. PATENT DOCUMENTS 5,607,845 A * 3/1997 Spira .................... C07K 14/755
435/173.8
6,420,140 B1 * 7/2002 Hori ....................... C07K 14/00
435/320.1
(Continued)

OTHER PUBLICATIONS

Bandaranayake et al., Recent Advances in Mammalian Protein Production, vol. 588, No. 2, NIH Public Access, Jan. 21, 2014, pp. 253-260.
(Continued)

*Primary Examiner* — Gailene Gabel
(74) *Attorney, Agent, or Firm* — Kilpatrick Townsend & Stockton LLP

(57) ABSTRACT

This invention provides improved cell lines for manufacture of protein-based pharmaceutical agents, considerably reducing the cost of commercial production. The cell lines are obtained by fusing cells from one or more parental cell populations. The hybrid cells are then selected for one or more characteristics that support protein production on a non-specific basis, such as the level of endoplasmic reticulum, Golgi apparatus, and/or other desired phenotypic features, compared with other hybrids or parental cells in the starting mixture. A gene encoding a therapeutic protein is transfected into the cells before or after one or more cycles of fusion and selection. Depending on the protein product being expressed, cell lines may be obtained that produce as much as eight grams or more of protein per liter of culture fluid.

19 Claims, 1 Drawing Sheet

(51) Int. Cl.
  *C12N 5/16* (2006.01)
  *G01N 33/569* (2006.01)
  *G01N 33/50* (2006.01)
(52) U.S. Cl.
  CPC ..... *C12P 21/005* (2013.01); *C12Y 301/03001* (2013.01); *G01N 33/5005* (2013.01); *G01N 33/5076* (2013.01); *G01N 33/56966* (2013.01); *C07K 2317/14* (2013.01); *C07K 2317/51* (2013.01); *C07K 2317/515* (2013.01); *C12N 2510/02* (2013.01); *G01N 2333/916* (2013.01)

(56) References Cited

U.S. PATENT DOCUMENTS 7,429,380 B2   9/2008   Hori et al.
9,816,110 B2   11/2017  Shen et al.

OTHER PUBLICATIONS

Huang et al., An Efficient and Targeted Gene Integration System for High-Level Antibody Expression, Journal of Immunological Methods, vol. 322, 2007, pp. 28-39.

Jayapal et al., Recombinant Protein Therapeutics from CHO Cells—20 Years and Counting, CHO Consortium, SBE Special Section, pp. 40-47, (2007).

Kim et al., CHO Cells in Biotechnology for Production of Recombinant Proteins: Current State and Further Potential, Applied Microbiology Biotechnology, vol. 93, 2012, pp. 917-930.

Lai et al., Advances in Mammalian Cell Line Development Technologies for Recombinant Protein Production, Open Access Pharmaceuticals, vol. 6, No. 5, AISSN 1424-8247, Apr. 26, 2013, pp. 579-603.

Lee et al., Site-Specific Integration in CHO Cells Mediated by CRISPR/Cas9 and Homology-Directed DNA Repair Pathway, Scientific Reports, vol. 5, No. 8572, Feb. 25, 2015, pp. 1-11.

Omasa et al., Cell Engineering and Cultivation of Chinese Hamster Ovary (CHO) Cells, Current Pharmaceutical Biotechnology, vol. 11, 2010, pp. 233-240.

Ronda et al., Accelerating Genome Editing in CHO Cells Using CRISPR Cas9 and CRISPy, a Web-Based Target Finding Tool, Biotechnology and Bioengineering, vol. 111, No. 8, Aug. 2014, pp. 1604-1616.

Al-Rubeai, Antibody Expression and Production, vol. 7, Cell Engineering, pp. 1-24, (2011).

Wilkens et al., Comparative Metabolic Analysis of CHO Cell Clones Obtained through Cell Engineering, for IgG Productivity, Growth and Cell Longevity, PLOS ONE, Mar. 13, 2015, pp. 1-15.

* cited by examiner

CELL LINES FOR HIGH LEVEL PRODUCTION OF PROTEIN-BASED PHARMACEUTICALS

REFERENCE TO RELATED APPLICATION

This application claims the priority benefit of U.S. provisional application 62/213,880, filed Sep. 3, 2015. The priority application is hereby incorporated herein by reference in its entirety for all purposes.

FIELD OF THE INVENTION

This application relates generally to the production of pharmaceutical compounds that are protein-based. It also relates to the modification and selection of cells and to transfection of such cells with a gene of interest to obtain cell lines for protein production at high productivity with improved biological and pharmacological characteristics.

BACKGROUND

Biological agents constitute a continually growing proportion of the market for pharmaceuticals. They have higher specificity than other agents, leading to more targeted efficacy with fewer side effects. With it comes a burgeoning need for improved means of industrial production, with greater productivity and lower cost.

Some therapeutic proteins have a therapeutic dose and dosing schedule that may require more than 10 grams of protein per patient per year. Current levels of protein production are generally no more than 4 g per liter of culture fluid, and are more typically less than 2 g per liter. To supply the market for a particular protein product, it may be necessary to produce 400,000 kg per year. This means that 100 million liters of culture medium would need to be processed—about the volume of 40 Olympic® sized swimming pools—which in turn would require several dedicated $1 billion manufacturing facilities.

Recent advances in mammalian protein production are discussed in A. D. Bandaranayake and S. C. Almo, FEBS Lett 2014, 588(2): 253-260; and T. Lai et al., Pharmaceuticals 2013, 6:579-603. Cell engineering and cultivation of Chinese Hamster Ovary (CHO) cells is reviewed in T. Omasa et al., Current Pharmaceutical. Biotechnology, 2010: 11, 233-240; C. A. Wilkens and Z. P. Gerdzen, PLOS ONE, Mar. 13, 2015; and J. Y. Kim et al., Appl. Microbiol. Biotechnol. 2012, 93:917-930. Multiplex genome engineering using systems such as CRISPR/Cas 9 is reviewed by L. Cong et al., Science 2013, 339(6121):819-823; Y. Huang et al., J. Immunol. Methods 2007, 322:28-39; J. S. Lee et al., Science Reports, Feb. 25, 2015; and P. Mali et al., Nat. Methods 2013, 10(10):957-963.

U.S. Pat. No. 5,607,845 (Spira et al., Pharmacia & Upjohn) proposed a method for obtaining an increased production of a producing cell line using a fusion protocol. U.S. Pat. No. 6,420,140 (Hori et al., Abgenix Inc.) proposed production of multimeric protein by a cell fusion method. Genome editing in CHO cells using CRISPR/Cas9 and CRISPy is reviewed by C. Ronda et al., Biotechnol. Bioeng. 2014, 111:1604-1616.

None of the technology described so far has the features and benefits of the technology of this invention, as described in the sections that follow.

SUMMARY OF THE INVENTION

According to current standards, production of therapeutic proteins (such as antibodies) is expensive, requiring large volumes of culture medium and complex infrastructure. This invention provides substantially increased protein production yields on a per-cell basis, reducing the cost of commercial production and potentially improving product quality.

Model cell lines of this invention are obtained by fusing cells from one or more parental cell lines or populations. The hybrid cells are screened for one or more characteristics that support protein production on a basis that is not specific for a particular protein: for example, the density of endoplasmic reticulum in the cell, the density of Golgi apparatus, and/or the level of other desired phenotypic features, compared with other hybrids or parental cells in the starting mixture. A gene encoding a therapeutic protein is transfected into the cells before, after, or during one or more cycles of fusion and selection. Depending on the chosen protein, cell lines may be obtained that produce as much as eight grams of protein per liter of culture fluid.

One aspect of this invention is a method of obtaining a cell line adapted for high-level production of protein-based pharmaceuticals. This includes culturing a mixture of cells under conditions whereby the mixture forms one or more cell hybrids, each comprising two or more cells from the mixture, and selecting cell hybrids from the mixture to obtain a producer cell population that is enriched for a higher density of one or more subcellular organelles that support increased production and/or secretion of protein, compared with other hybrids or parental cells in the starting mixture. The mixture may consist essentially of cells from a single cell line, or two or more different cell lines, exemplified by Chinese Hamster Ovary (CHO) cells.

The method for selecting suitable hybrids may include one or more of the following procedures:
  selecting cell hybrids that have a relatively high density of endoplasmic reticulum per cell, compared with other hybrids or parental cells in the mixture;
  selecting cell hybrids that have a relatively high density of Golgi apparatus, compared with other hybrids or parental cells in the mixture;
  incubating cells with a vital dye that stains endoplasmic reticulum and/or Golgi, and sorting cell hybrids according to the amount of the vital dye associated with each hybrid; and
  expressing a fusion protein in cells in the mixture, wherein the fusion protein contains a peptide that generates an optical signal (such as GFP or luciferase) fused with a peptide that is processed by the endoplasmic reticulum and/or the Golgi apparatus, whereupon cells can be selected that express the optical signal at a higher level than other cells in the mixture.

The method for obtaining the cell line may further comprise one or more of the following procedures:
  selecting cell hybrids that grow better under specified culture conditions;
  binding the cell hybrids with antibody specific for a cell surface ligand (the antibody optionally labeled or linked to a particle), and selecting cell hybrids labeled with the antibody, thereby obtaining a subpopulation that is enriched for cell hybrids that express the ligand;
  electing cell hybrids that produce a relatively high level of a marker protein, compared with other cell hybrids in the mixture, wherein the marker protein is secreted from the cell and/or expressed on the cell surface, such as secreted alkaline phosphatase or secreted luciferase;
  selecting cell hybrids that produce a preferred glycosylation pattern or density on a marker protein, compared with other cell hybrids in the mixture; and culturing the producer cell population; and re-sorting cell hybrids therein for the same feature, thereby obtaining a subpopulation that is enriched for cell hybrids in which an increased density of the subcellular organelles is stably inheritable.

A producer cell line can be established from the producer cell population: for example, by transfecting cells from the producer cell line with a gene of interest to obtain a transfected cell population, and selecting transfected cells from the population that produce high levels of a protein product of the gene of interest, compared with other cells in the transfected cell population; or by selecting cell hybrids that produce a high level of protein product expressed from the gene of interest, compared with other cell hybrids in the mixture, and then establishing a producer cell line from the selected cell hybrids. The gene of interest can be inserted into the genome of the cells from the producer cell line or the mixture at a location that is pre-selected as permitting or supporting a high level of transcription, compared with other locations in the genome.

By way of example, the gene of interest may encode an antibody heavy chain, an antibody light chain, or a single-chain antibody. The producer cell line may express both an antibody heavy chain and an antibody light chain that combine to produce an antibody having a desired specificity. The producer cell line may express a therapeutic enzyme, a hormone, a growth factor, or a protein that is a naturally occurring component of blood. Depending on the circumstances, the producer cell line may optimally express at least eight grams of protein per liter of culture fluid from one or a combination of recombinantly inserted genes.

Another aspect of the invention is a method of producing a protein-based pharmaceutical. A cell line is obtained that has been adapted for high density manufacture by a process as outlined above, wherein the gene of interest encodes part or all of the protein, and culturing the cell line under conditions whereby the protein or a portion thereof is expressed from the gene of interest.

Another aspect of the invention is a hybrid cell line that contains part or all of the genome of two or more parental cell lines, a higher concentration of endoplasmic reticulum and/or Golgi apparatus compared with any of the parental cell lines, and a capacity to produce at least eight grams of protein per liter of culture fluid from one or a combination of recombinantly inserted genes.

Aspects of the invention that are of current commercial interest to the inventors are indicated by the appended claims. Other aspects of the invention will be apparent from the description that follows.

DETAILED DESCRIPTION

Context

Figure 1:
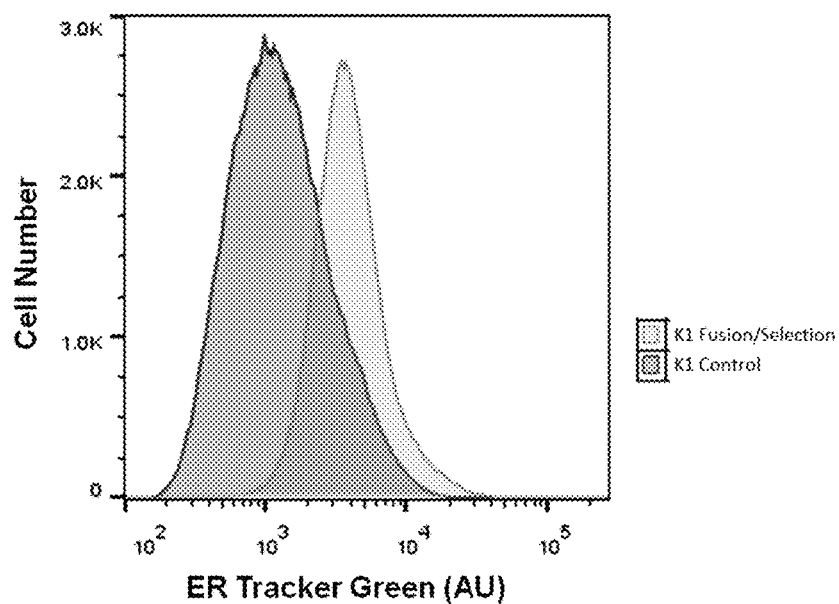
FIG. 1 shows the cell frequency profile for endoplasmic reticulum (ER) staining in native CHO cells, compared with CHO cell autotypic hybrids.

New biopharmaceutical products are coming on line at the rate of over 100 per year, while competition in the production of biosimilars continues to increase. There is a clear need for technology that can reduce the culture volume and cost required for production of these products.

This invention provides technology that allows product of protein biologicals at a productivity that surpasses current standards: Potentially as much as 8 g per liter or more. The high efficiency producer cell lines of this invention can be used for industrial applicability in several ways. Regarding biosimilars, companies with brand-name products could maintain a marketing advantage by lowering their product cost structure. Similarly, companies producing biosimilars would compete with the brand-name products on cost. The cell lines provide considerable production flexibility by increasing capacity of existing plants; allowing production of more protein from fewer or smaller facilities; and reducing cost and time-to-clinic for new products.

Making Cell Hybrids

The makers of this invention have discovered that cells suitable for protein production can attain a higher level of production by fusing with other cells. Without limiting practice of the invention, it is hypothesized that fusing two cells together is partly additive in terms of the components, genetics, or genetic control of the cells that participate in protein production. It is beneficial if the improved characteristics breed true. Accordingly, after cells are fused, they are typically subject to multiple rounds of culturing and selection for phenotypic characteristics of interest.

Model cells suitable for fusion are cell lines that have already been employed for industrial protein production, such as CHO cells, mouse myeloma NS0 cells, mouse myeloma SP2/0 cells, Human Embryonic Kidney (HEK) 293 cells, and Baby Hamster Kidney (BHK-21) cells. Also suitable are other Chinese Hamster cell types (for example, breast and liver cells that make secreted protein), human cell lines, and invertebrate cells, such as insect and mollusk cells that may have desired glycosylation properties. The cells are fused together by obtaining a cell mixture of cells to be fused (typically a plurality of cells from one cell line, or more than one cell line), and then subjecting the mixture to an appropriate fusion protocol: for example, conducting an electrofusion, combining with a fusogenic virus such as Sendai virus, or by treating with polyethylene glycol.

For purposes of this disclosure, cells that have been made by fusing two or more cells together may be referred to as autotypic hybrids (cells from the same cell line fused together), isotypic hybrids (cells having the same genotype), allotypic hybrids (cells from different individuals of the same species having different genotypes), and xenotypic hybrids (cells from different species). Autotypic hybrids are typically formed using a population of cells that consists essentially (that is, at least 99%) of cells from a single cell line. The other types of hybrids are typically formed using cell populations from two or more cell lines which have potentially complementary properties. The invention also includes the fusion of one or more cell populations from primary sources with themselves or with established or cloned cell lines.

Typically a fused cell is obtained by fusing two cells together, although fusion of three or more cells is possible. It is recognized that fusion of two different cell populations will result in mixed cell products (isotopic, allotypic, or xenotypic hybrids, depending on the parental cell lines), and autotypic hybrids. Autotypic or isotypic hybrids can be separated from allotypic or xenotypic hybrids, if desired, using fluorescently labeled or surface bound antibody specific for a ligand expressed on one of the cell lines in the mixture, but not another.

All such combinations come within the scope of this invention, unless explicitly indicated otherwise. It may be beneficial to repeat the cell fusion within a population of hybrids to enhance the effect further, and/or cross-hybridize with other cell lines to imbue the ultimate cell line with additional beneficial characteristics. Thus, the fusion and selection steps may be done iteratively twice, three or four times, or more.

Selecting High Producer Cell Lines

An important insight of this invention is the idea that protein production can be increased by selecting cell hybrids for higher levels subcellular machinery or biochemistry that support increased protein production, compared with other hybrids or parental cells in the starting mixture. At least one of the phenotypic features is selected that is not specific for production of a particular protein. The feature is not simply the level of expression of a protein of interest or a surrogate. Rather, it is a feature that supports production of a wide range of different proteins. Such features include the relative density of subcellular organelles, particularly those involved in secretion of protein from the cell, and the relative level or concentration of enzymes that help finish or secrete a variety of different proteins.

Subcellular organelles involved in secretion of protein include the endoplasmic reticulum (ER) and the Golgi apparatus. Either or both of these can be measured and used as a basis for sorting or selection without damaging the cell using a vital dye, and the cells can be selected on the basis of the amount of dye that is associated.

Such dyes can be obtained commercially, for example from the company Molecular Probes. Examples of vital dyes for ER include:

ER-Tracker™ Blue-White DPX (E12353)
ER Tracker™ Green (glibenclamide BODIPY® FL) (E34251)
ER-Tracker™ Red (glibenclamide BODIPY® TR) (34250)
$DiOC_6$ (D273)
$DiOC_5$ (D272).

Vital dies for Golgi apparatus include:

NBD C6-6-ceramide (N1154)
BODIPY® FL C5-cerimide (D3521)
BODIPY® TR ceramide (D7540)

Alternatively or in addition, the user can test expression-based labeling systems that would introduce a fluorescent protein targeted to ER or Golgi. They are fusion proteins comprising a portion that expresses an optical label, fused with a protein sequence that targets or is processed by the organelle to be labeled. Examples include the following:

Invitrogen:
  CellLight™ ER-GFP (C10590)
  CellLight™ ER-GFP (C10591)
  CellLight™ Golgi-GFP (C10592)
  CellLight™ Golgi-GFP (C10593)
Evrogen:
  pmKate2-ER (FP324)
  pFusionRed-ER (FP420)
  pTagRFP-Golgi (FP367)
  pFusionRed-Golgi (FP419)
Clontech:
  pDsRed2-ER Vector (632409)
  pDsRed-Monomer-Golgi Vector (632480)
  pAcGFP1-Golgi Vector (632464)

After staining with any of these dyes, cells may be selected (for example, by flow cytometry and sorting) that have on average a level of staining that is at least 1.2, 1.5, 2, or more than 2-fold higher than the parental cell line or lines, in terms of staining, for example, for ER, Golgi, or an optically labeled gene product.

Other features to select for may include but are not limited to phenotypic features, immunological features, and levels of protein production. Immunological features may include expression of a desired ligand by the cell (for example, secreted by the cell or expressed on the surface). Cells having an average level of expression of such markers that is at least 1.5, 2, 3, or 5-fold higher than the parental line can be selected, for example, by direct or indirect antibody labeling followed by FACS, or by binding to and releasing from antibody-coated microbeads. Immunological markers of interest include ligands that participate in production of secreted protein, such as glycosylation enzymes. Other sorting methods that can be used to screen fused cells according to this invention may include PCR-activated cell sorting, fluorescence in situ hybridization flow cytometry (FISH-PC), or FISH followed by laser capture.

The cell hybrids can also be selected for features that are desired for manufacturing purposes: such as cell hybrids that grow better under specified culture conditions, or that express relatively lower levels of one or more undesired contaminants.

To generate a cell line that is sufficiently stable to be used for manufacturing, the selected cells can be grown in culture through several cell divisions, and then re-tested to see if the desired feature is stable, for a total of two, three, or more than three times for each desired feature.

Transfecting Cells with a Gene of Interest

To generate a cell line expressing a protein of interest, hybrids that have been selected for ER, Golgi, and/or any of the features listed above can be transfected with a gene encoding the protein under control of a ubiquitous or mammalian promoter that causes expression in the host cell line. The level of protein production can be determined in the course of processing using a transient transfection method to insert a protein expression cassette. Alternatively or subsequently, permanent transfection can be done that integrates the gene of interest or a marker gene into the genome of the cell line. Transfection can be done using liposome-based reagents (for example, Lipofectamine™ 2000 or FuGENE™ 6), calcium phosphate, electroporation, or infection with an adenovirus, retrovirus or lentivirus based vector.

Following transfection, the cells are tested for production or secretion of the gene of interest (typically after cloning or limiting dilution culture): for example, by enzyme-linked immunosorbant assay (ELISA). Cells or clones having increased production of the desired protein are selected. The objective can be an increase in protein production that is 1.5, 2, 4, 8, 12, 16, or 20-fold higher than the parental cell line; and/or production at a level of 6 g, 8 g, 10 g, 12 g, 15 g, or 20 g per liter of culture fluid under typical manufacturing conditions. The protein of interest can also be tested for other desired characteristics, such as the quality of sialylation or other aspects of glycosylation.

In principle, the transfection can be done either before, during, or after one or more cycles of fusion and selection for other features. For example, the fusion and selection can be done before transfection with the gene of interest, thereby establishing a parental cell line suitable for high-level production of a protein of the user's choice. Alternatively, the transfection can be done into the parental cell line, and used to track production levels during subsequent fusion and sorting steps, or to provide another basis for such sorting. Alternatively, the transfection can be done as an intermediate step, wherein the cells have already been subject to one or more cycles of fusion and selection for some other feature such as ER or Golgi, the resulting hybrid is transfected to express a protein of interest, and then subjected to further cycles of fusion and selection for expression of the protein of interest and/or other features referred to earlier in this disclosure.

The protein of interest can be the biological agent that is intended for manufacture: for example, an antibody heavy chain, an antibody light chain, a single-chain antibody, a therapeutic enzyme, a hormone, a growth factor, or a protein that is normally a blood component.

Another option is to develop a cell line according to this invention using a marker protein as a proxy for the protein that ultimately will be manufactured: for example, secreted alkaline phosphatase or secreted luciferase. Again, the transfection can be done before, during, or after multiple cycles of fusion and selection, optionally using the level of expression of the marker as the selection criteria in one or more of the cycles. This creates a parental cell line that is optimized for expression of the marker protein, with the expectation that the beneficial characteristics of the cell line will be retained after further genetic alteration.

Ultimately, once a cell line has been developed having a desired level of expression of the marker protein, the marker is then replaced with the protein of interest. Transfection can again be done randomly into the genome, using the techniques listed above, and expression of the marker protein is curtailed. Alternatively, the gene for the marker protein can be substituted with a gene that encodes the protein of interest using a targeted integration technique. Such techniques comprise, for example, CRISPR/Cas9, a zinc-finger recombinase (ZFR), or a transcription activator-like effector nuclease (TALEN). That way, the gene of interest is inserted into the genome of the cells from the producer cell line or the mixture at a location that is pre-selected as permitting or supporting a high level of transcription, compared with other locations in the genome.

For more information on the use of targeted integration techniques, the reader may refer to L. Cong et al., Science 2013, 339(6121):819-823; Y. Huang et al., J. Immunol. Methods 2007, 322:28-39; J. S. Lee et al., Science Reports, Feb. 25, 2015; and P. Mali et al., Nat. Methods 2013, 10(10):957-963; and C. Ronda et al., Biotechnol. Bioeng. 2014, 111:1604-1616.

Other Methodology

The system and techniques provided in this disclosure can be combined with one or more alternative strategies to enhance cell growth or protein production for purposes of manufacture. Such techniques include vector and expression platform engineering, omics-based approaches, advances in gene delivery and integration, enhancement of protein production using chromatin opening elements, improvements in clone screening strategy, and so on.

Such techniques are discussed, for example, in A. D. Bandaranayake and S. C. Almo, FEBS Lett 2014, 588(2): 253-260; T. Lai et al., Pharmaceuticals 2013, 6:579-603; T. Omasa et al., Current Pharmaceutical. Biotechnology, 2010: 11, 233-240; C. A. Wilkens and Z. P. Gerdzen, PLOS ONE, Mar. 13, 2015; J. Y. Kim et al., Appl. Microbiol. Biotechnol. 2012, 93:917-930; and C. Ronda et al., Biotechnol. Bioeng. 2014, 111:1604-1616.

Benefits of the Invention

Depending on the mode of practice and application, the invention described in this disclosure can provide any of the following benefits in any combination:

reduce the need to enlarge or build new GMP production facilities as market size increases;

provide GMP production of kilogram quantities of finished protein product with relatively small or fewer bioreactors, reduce the cost of production of proven biological agents;

create production cell lines suitable for high-level expression of a family of desired biological agents;

decrease cloning or selection steps that are needed following integration of the gene to be expressed;

improve product quality (for example, glycosylation); and provide high quality low volume research materials, reducing the time to clinical trials.

EXAMPLES

Example 1

The invention can be practiced using the K1 line of CHO cells as follows. A population of CHO cells is fused so as to make isotopic hybrids according to the following protocol:

1. Centrifuge $10^7$ cells.
2. Discard supernatant
3. Break the pellet by gently tapping the bottom of the tube
4. Add 100 µL of 50% PEG over the period of one minute, while mixing the cells with a pipette tip
5. Continue stirring the cells for one additional minute
6. Add 100 µL of growth medium over one minute while mixing
7. Add 300 µL of growth over three minutes while mixing
8. Slowly add mL. of growth medium
9. Incubate at 37 deg C. for five minutes
10. Centrifuge
11. Re-suspend the pellet in 20 mL of growth medium and transfer to a 125-mL culture flask
12. Culture normally Alternatively, an electrofusion procedure is employed using ECM2001 pulse generator (BTX). $10^7$ cells are centrifuged and resuspended in 1 mL of Cytofusion™ Medium C, then transferred into the fusion chamber. Cells are aligned with an alternating current pulse of 150 V/cm for 10 seconds. Cell fusion is triggered by a single square wave direct current pulse of 1200 V/cm for 25 µsec. Cells are allowed to rest for 5 min., centrifuged, then resuspended in growth medium and cultured normally.

Alternatively, a virus-induced fusion protocol may be employed. Various protocols exist using Sendai virus: for example, using a GenomONE™ HVJ-E Kit (Cosmo Bio USA): Cells are centrifuged and resuspended in ice cold cell fusion buffer at $2 \times 10^5$ cells/25 µL. 2.5 µL of an ice-cold HVJ-E (Sendai virus membranes) suspension is added to the cells and mixed by tapping. Mixture is incubated on ice for 5 min; then at 37 deg C. for 15 min. Growth medium is added to the mixture and it is transferred into a six-well plate for culture.

Labeling and sorting for subcellular organelles can be done as follows. The cells are centrifuged and washed once with HBSS buffer. A 1 µM solution of ER-tracker Green and/or ER-tracker Blue/White is prepared in HBSS. The cells are re-suspended in staining solution and incubated at 37 deg C. for 30 minutes. The cells are then washed with PBS.

If cells are to be used for analytical FACS, they are re-suspended in PBS; if they are to be sorted, they are re-suspended in PBS supplemented with 1% FBS. Ten percent of the viable population exhibiting the highest amount of staining with ER-Tracker dye was collected. The cells are collected into tubes containing growth medium, centrifuged, re-suspended in fresh medium, and then cultured normally.

Example 2

CHO-K1 cells were exposed to a PEG-assisted fusion procedure. The cells were allowed to recover for one week, then the procedure was repeated for a total of three times. Following recovery from the third fusion, the cells were stained with vital ER-tracking dye (ER-Tracker™ Green (glibenclamide BODIPY® FL); Invitrogen, E34251) and sorted using a FACSAriaII™ cell sorter (BD Biosciences). Ten percent of the viable population exhibiting the highest amount of staining with ER-Tracker dye was collected. Following a two-week recovery in culture, the cells were exposed to a final fusion, stained with ER-tracking dye, and analyzed using a LSRII™ flow cytometer (BD Biosciences).

To measure protein production in the fused cells, and the parental CHO population, the cells were transfected to express secreted alkaline phosphatase (SEAP). The transfection was performed as follows:
1. Centrifuge $10^6$ cells.
2. Discard supernatant
3. Resuspend in 100 µL Cell Line Nucleofector™ Solution T
4. Add 2 µg SEAP expression plasmid
5. Transfer to electroporation cuvette
6. Electroporate using Amaxa™ Nucleofector II and preset program U-023
7. Add 0.5 ml growth medium
8. Transfer cells into 6-well plate containing mL. growth medium per well FIG. 1 is the FACS (florescence-activated cell sorting) profile of the CHO cells after fusion and staining for levels of endoplasmic reticulum (ER). Fused cells showed a higher average level of ER compared with the starting CHO cell line.

Figure 2:
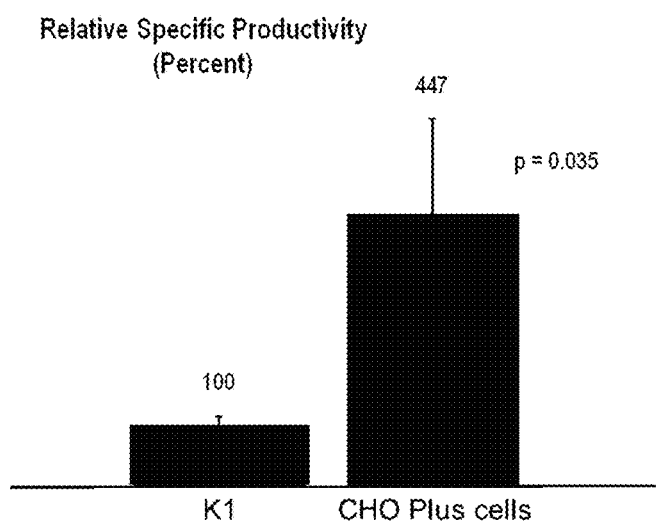
FIG. 2 shows the relative level of expression of alkaline phosphatase transfected into native CHO cells, compared with CHO cell autotypic hybrids. The expression in the fused cells is shows over 4-fold improvement ($p<0.05$).

FIG. 2 shows the transfection results (specific productivity of secreted alkaline phosphatase). The expression of the marker protein in the fused cells is shows over 4-fold improvement.

For all purposes in the United States of America, each and every publication and patent document referred to in this disclosure is incorporated herein by reference in its entirety for all purposes to the same extent as if each such publication or document was specifically and individually indicated to be incorporated herein by reference.

While the invention has been described with reference to the specific embodiments, changes can be made and equivalents can be substituted to adapt the invention to a particular context or intended use as a matter of routine experimentation, thereby achieving benefits of the invention without departing from the scope of what is claimed.

The invention claimed is:

1. A method of obtaining a cell line adapted for high-level production of protein-based pharmaceuticals, comprising:
   (a) culturing a mixture of cells under conditions whereby the mixture forms one or more cell hybrids, each comprising two or more cells from the mixture; then
   (b) sorting the mixture of cells according to the density of endoplasmic reticulum and/or Golgi apparatus per cell; and
   (c) selecting and recovering cell hybrids from the mixture that have a relatively high density of endoplasmic reticulum and/or Golgi apparatus per cell; thereby obtaining a producer cell line that supports increased production and/or secretion of protein compared with other hybrids or parental cells in the starting mixture.

2. The method of claim 1, wherein the mixture cultured in step (a) consists essentially of cells from a single cell line.

3. The method of claim 1, wherein the mixture cultured in step (a) comprises two or more different cell lines.

4. The method of claim 1, wherein the mixture comprises Chinese Hamster Ovary (CHO) cells.

5. The method of claim 1, wherein step (c) includes selecting and recovering cell hybrids that have a relatively high density of endoplasmic reticulum per cell, compared with other hybrids or parental cells in the mixture.

6. The method of claim 1, wherein step (c) includes selecting and recovering cell hybrids that have a relatively high density of Golgi apparatus, compared with other hybrids or parental cells in the mixture.

7. The method of claim 1, wherein step (b) includes incubating cells with a vital dye that stains endoplasmic reticulum and/or Golgi, and sorting cell hybrids according to the amount of the vital dye associated with each hybrid.

8. The method of claim 1, further comprising binding the cell hybrids with antibody specific for a cell surface ligand, and selecting cell hybrids labeled with the antibody, thereby obtaining a subpopulation that is enriched for cell hybrids that express the ligand.

9. The method of claim 1, further comprising selecting cell hybrids that produce a relatively high level of a marker protein, compared with other cell hybrids in the mixture, wherein the marker protein is secreted from the cell and/or expressed on the cell surface.

10. The method of claim 1, further comprising selecting cell hybrids that produce a specific glycosylation pattern that express a specific marker protein, compared with other cell hybrids in the mixture.

11. The method of claim 1, further comprising culturing the producer cell population; and are sorting cell hybrids therein according to the density of endoplasmic reticulum and/or Golgi apparatus in the cell hybrids, thereby obtaining a subpopulation that is enriched for cell hybrids in which an increased density of the subcellular organelles is stably inheritable.

12. The method of claim 1, further comprising transfecting cells from the producer cell line with a gene of interest to obtain a transfected cell population, and selecting transfected cells from the transfected cell population that produce high levels of a protein product of the gene of interest, relative to other cells in the transfected cell population.

13. The method of claim 12, wherein the gene of interest encodes an antibody heavy chain, an antibody light chain, or a single-chain antibody.

14. The method of claim 12, wherein the producer cell line expresses both an antibody heavy chain and an antibody light chain that combine to produce an antibody having a desired specificity.

15. The method of claim 12, wherein the producer cell line expresses a therapeutic enzyme, a hormone, a growth factor, or a protein that is a naturally occurring component of blood.

16. The method of claim 12, wherein the producer cell line expresses at least eight grams of protein per liter of culture fluid from one or a combination of recombinantly inserted genes.

17. A method of obtaining a cell line adapted for high-level production of protein-based pharmaceuticals, comprising:

(a) culturing a mixture of cells under conditions whereby the mixture forms one or more cell hybrids, each comprising two or more cells from the mixture; then (b) expressing a fusion protein in cells in the mixture, wherein the fusion protein contains a fluorescent or bioluminescent peptide that generates an optical signal fused with a peptide that is processed by endoplasmic reticulum and/or Golgi apparatus; and (c) selecting and recovering cells that express the optical signal at a higher level relative to other cells in the mixture;

thereby obtaining a producer cell line that supports increased production and/or secretion of protein compared with other hybrids or parental cells in the starting mixture.

18. A hybrid cell line, comprising part or all of the genome of two or more parental cell lines, a higher concentration of endoplasmic reticulum and/or Golgi apparatus relative to any of the parental cell lines, and a capacity to produce at least eight grams of protein per liter of culture fluid from one or a combination of recombinantly inserted genes.

19. A method of producing a protein for compounding as a biopharmaceutical, the method comprising:

obtaining cells from a hybrid cell line according to claim 18, wherein the recombinantly inserted gene(s) encode part or all of the protein, and culturing the cells under conditions whereby the protein or a portion thereof is expressed by the cells from the recombinantly inserted gene(s).

* * * * *